US010413220B2

(12) United States Patent
Ling et al.

(10) Patent No.: US 10,413,220 B2
(45) Date of Patent: Sep. 17, 2019

(54) LIMB MOVEMENT FUNCTION EVALUATING METHOD AND IMPLANTATION SYSTEM THEREOF

(71) Applicant: National Cheng Kung University, Tainan (TW)

(72) Inventors: Shih-Fu Ling, Tainan (TW); Fong-Chin Su, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 347 days.

(21) Appl. No.: 15/160,241

(22) Filed: May 20, 2016

(65) Prior Publication Data

US 2017/0042455 A1 Feb. 16, 2017

(30) Foreign Application Priority Data

Aug. 10, 2015 (TW) ............................ 104125881 A (51) Int. Cl.
*A61B 5/11* (2006.01)
*A61B 5/00* (2006.01)

(52) U.S. Cl.
CPC .......... *A61B 5/1124* (2013.01); *A61B 5/1121* (2013.01); *A61B 5/1122* (2013.01); *A61B 5/1126* (2013.01); *A61B 5/6867* (2013.01); *A61B 5/702* (2013.01); *A61B 5/7225* (2013.01); *A61B 2505/09* (2013.01)

(58) Field of Classification Search
CPC .... A61B 5/1121; A61B 5/1122; A61B 5/1124
See application file for complete search history.

(56) References Cited

U.S. PATENT DOCUMENTS

2010/0069798 A1* 3/2010 Cheng .................. A61F 5/0102
601/5

FOREIGN PATENT DOCUMENTS

JP 10248814 A * 9/1998

OTHER PUBLICATIONS

English Translation of JP-10248814-A (Year: 1998).*

* cited by examiner

*Primary Examiner* — Daniel L Cerioni
*Assistant Examiner* — Yasmeen S Warsi
(74) *Attorney, Agent, or Firm* — Chun-Ming Shih (57) ABSTRACT

A limb movement function evaluating method and the implantation system are provided. The aforementioned system includes a limb fixing device, limb guiding device, driver, actuator, impedance detector, and movement function analyzer. The limb fixing device is used to fix the first end of the user limb. The driver is used to guide the second end of the user limb through the actuator so as to make the second end moving relatively to the first end. The impedance detector is further connected to the driver so as to measure mechanical impedance where the movement of the user limb responses to the driving point of the driver. Finally, the limb movement analyzer compares the measured mechanical impedance and the movement path of the user limb so as to form a limb movement function curve. Therefore, the medical staff can make accurate rehabilitation evaluation according to the limb movement function curve.

2 Claims, 7 Drawing Sheets

LIMB MOVEMENT FUNCTION EVALUATING METHOD AND IMPLANTATION SYSTEM THEREOF

This application claims priority benefit of TW Patent Application Ser. No. 104125881 filed Aug. 10, 2015 which is hereby incorporated herein by reference its entirety.

BACKGROUND OF THE INVENTION

1. Field of the Invention

The present disclosure relates to a limb movement function evaluating method and an implantation system thereof, particularly the method and the system thereof providing various limb movement paths and intensity in rehabilitation training and evaluating limb movement functions by analyses of mechanical impedances responding to limb movement driven by an electrical device at driving points.

2. Description of the Prior Art

A person whose limb or nervous system is impaired in an accident or a disease may suffer dyskinesia or fail to have normal activities. Currently, the impairment of a limb or the nervous system is evaluated with the Ashworth Scale which is a simple but neither objective nor accurate method.

For the efficacy of convalescent therapy, an existing course of treatment for rehabilitation is mostly dependant on a physiotherapist who artificially guides a patient's limb to move. In this regard, rehabilitation needs vast specialized manpower and medical costs. However, the existing methods for rehabilitation impose huge burdens on both patients and health care resources.

Some conventional rehabilitation devices which are operated by patients themselves are characteristic of guiding a convalescent's limb for rehabilitation; however, a convalescent has to take advantage of multiple devices for rehabilitation because each of these devices features a single movement path or exercise way. Moreover, these devices fail to evaluate real-time variations of limb functions objectively and adjust intensity of rehabilitation training as well as any movement path for a limb according to a convalescent's rehabilitation status. These drawbacks abate the efficacy of convalescent therapy and result in intervention of rehabilitation specialists.

It can be seen from literatures that conventional sensors such as torsion meters and velocity sensors had been installed on convalescents' limbs by some American and European medical technology research units in recent years to measure limb movement functions. However, some problems such as significant error or difficulty in usage attributed to the load effect of a sensor or a sensor which was difficultly fixed on a limb had occurred in these methods. In addition, errors existed in measurement data because the concept of mechanical impedance was not properly applied in those researches as shown in the published literatures. Against this background, there is still no proper instrument which is available to clinic applications.

With the previous descriptions summarized, it is a technical issue of persons skilled in the art to provide a rehabilitation device which needs not to install extra components on a convalescent's limb but accurately quantifies a convalescent's limb movement functions and satisfies a convalescent with multiple rehabilitation options and intensity for different adjustments based on updated rehabilitation status of a convalescent.

SUMMARY OF THE INVENTION

To settle the previous technical issues, the present disclosure is intended to provide a limb movement function evaluating method and an implantation system thereof by which a convalescent's limb is guided to complete various repeated motions and rehabilitation status of a limb is evaluated and analyzed.

To this end, a limb movement function evaluating system in the present disclosure comprises a limb fixing device, a limb guiding device, a driver, an actuator, an impedance detector and a movement function analyzer. The limb fixing device is used in fixing a first end of an external user limb, the limb guiding device is used in guiding a second end of a user limb, and the second end and the first end are separated from each other by a distance. The driver relies on the actuator to drive the limb guiding device for movement of the second end relative to the first end. The impedance detector linking the driver is used to measure mechanical impedances corresponding to reactions of a driven limb. The movement function analyzer which links the impedance detector provides information of a limb movement function curve according to measured mechanical impedances corresponding to a movement path of a user limb.

To this end, a limb movement function evaluating method in the present disclosure is applied to a limb movement function evaluating system and comprises steps as follows: (1) Fix the first end of a user limb. (2) Guide the second end of the user limb for movement relative to the first end. (3) Measure mechanical impedances responding to user limb movement at driving points. (4) Provide a limb movement function curve according to measured mechanical impedances which correspond to a movement path of the user limb.

To this end, a computer device for analyzing limb movement functions is offered in the present disclosure. The computer device comprises a communicator and a processor. The communicator communicates with at least a limb movement function evaluating system through a wired communications network or a wireless communications network. The processor which links the communicator is able to access a plurality of limb movement function curves from at least a limb movement function evaluating system for statistic analyses and provide rehabilitation determining information by which a rehabilitation degree represented by the limb movement function curve is determined.

To this end, a method for analyzing limb movement function rehabilitation degree is applied in a computer device, which communicates with at least a limb movement function evaluating system, and comprises steps as follows: (1) Access a plurality of limb movement function curves. (2) Create statistics related to the limb movement function curves and provide information to determine rehabilitation status.

To this end, a computer program product embodied on a non-transitory computer readable medium and applied in a computer device is offered in the present disclosure wherein the computer device in which the computer program product is loaded and executed completes steps in the method for analyzing limb movement function rehabilitation degree.

In summary, a limb movement function evaluating system and an implantation system thereof analyze mechanical impedances responding to movement of a user limb, quantify rehabilitation status of a limb correctly, and provide quantified limb movement function curves to a user or the medical staff for determinations or analyses of rehabilitation status without drawbacks of the medical staff's defective and subjective judgment in conventional techniques.

BRIEF DESCRIPTION OF THE DRAWINGS

For a better understanding of the aforementioned embodiments of the invention as well as additional embodiments thereof, reference should be made to the Description of Embodiments below, in conjunction with the following drawings in which like reference numerals refer to corresponding parts throughout the figures.

DETAILED DESCRIPTION OF THE PREFERRED EMBODIMENT

The following description is about embodiments of the present invention; however it is not intended to limit the scope of the present invention.

Figure 1:
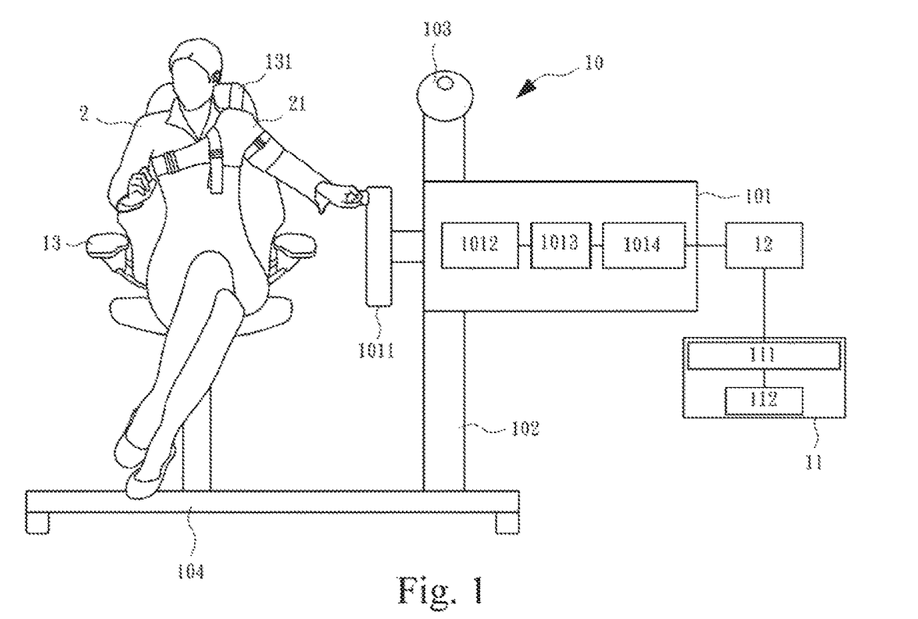
FIG. 1 is a schematic view of a limb movement function evaluating system.

Referring to FIG. 1, which illustrates a limb movement function evaluating system. The limb movement function evaluating system comprises a limb movement function evaluating device 10, an analysis device 11 and a carrying device 13 which supports a user 2. The carrying device 13 is provided with a limb immobilization module which is used in fixing a first end at a limb of the user 2. In detail, a support 21 is installed at a first end of a limb of the user 2; the limb immobilization module links the carrying device 13 and a drawstring 131 of the support 21.

Figure 2:
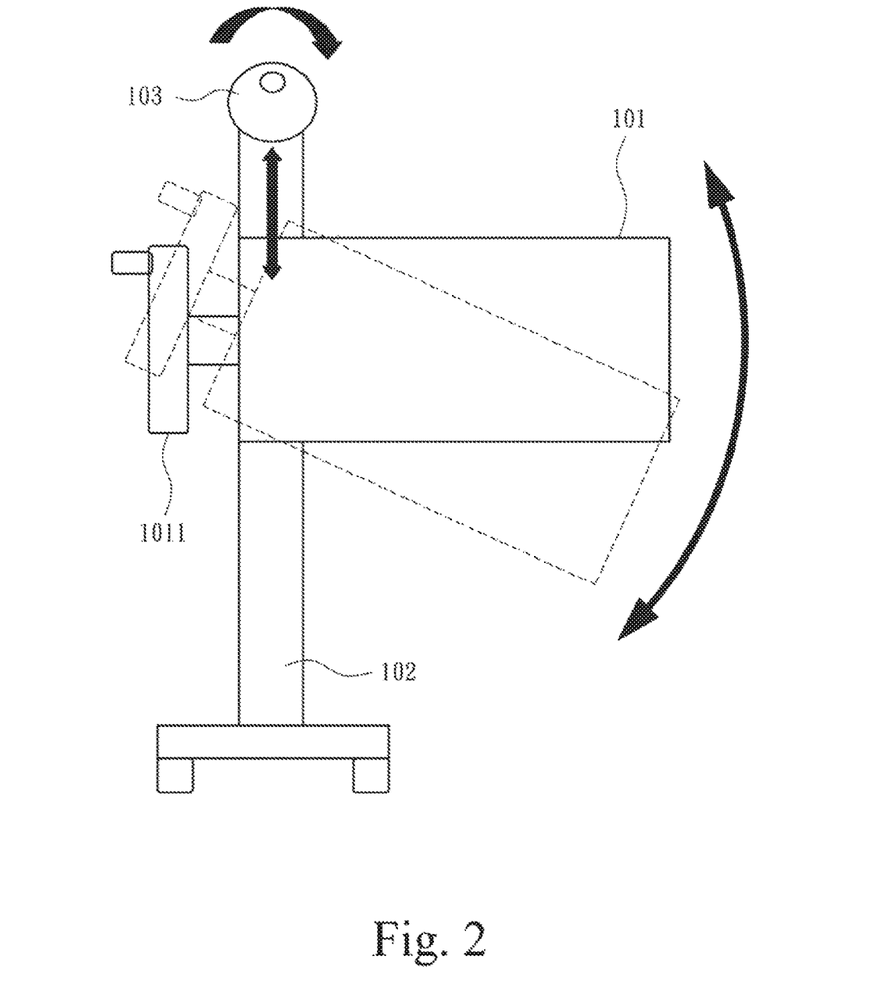
FIG. 2 is a schematic view of a limb movement function evaluating device which is adjusted in operation.

The limb movement function evaluating device 10 comprises a limb driving subsystem 101, a supporting portion 102, an adjustable handle 103 and a base 104. The adjustable handle 103 and the base 104 are installed at two ends of the supporting portion 102, respectively; the limb driving subsystem 101 is movably mounted on the supporting portion 102; the carrying device 13 and the supporting portion 102 share the base 104. Referring to FIG. 2, which illustrates the limb driving subsystem 101 is adjusted in height by a user 2 upward or downward with the adjustable handle 103 and an angle of the limb driving subsystem 101 relative to the supporting portion 102 is adjustable (0~90 degrees upward (downward) from a horizontal reference surface) or the limb driving subsystem 101 is rotated about the supporting portion 102.

The limb driving subsystem 101 comprises a limb guiding device 1011, an actuator 1012, a driver 1013 and an impedance detector 1014. The driver 1013 relies on the actuator 1012 to drive the limb guiding device 1011; the limb guiding device 1011 is used in guiding a second end at a limb of the user 2 to move in a space. The first end and the second end at a limb of the user 2 are separated from each other by a distance. The driver 1013 is a variable-speed motor, for example, a discontinuous variable-speed motor or a continuous variable-speed motor. The impedance detector 1014 linking the driver 1013 converts measured electrical signals from the driver 1013 to mechanical impedances corresponding to limb reactions.

For an arm as a user's limb, the first end and the second end could be a shoulder and a palm, respectively; for a leg as a user's limb, the first end and the second end could be the bottom (or the waist) and a sole, respectively. The above descriptions explain relationships between the first and second ends but do not limit the scope of the first and second ends.

The analysis device 11 is a computer device. The analysis device 11 comprises a movement function analyzer 111 and a displayer 112. The movement function analyzer 111 is connected to the displayer 112. The analysis device 11 is electrically connected to the impedance detector 1014 via the message communicating device 12 and receives measured impedances for following analyses.

When the limb movement function evaluating system runs, the driver 1013 relying on the actuator 1012 and the limb guiding device 1011 drives the second end at a limb of the user 2 to make a uniform movement or an approximate uniform movement relative to the first end. In virtue of various factors such as shapes, directions and tensions of bones, muscles, tendons and fascias, a mechanical impedance at a driving point is induced from a limb under guidance and analyzed in the analysis device 11 for elements (for example, mass (m), stiffness value (k) or damping value (c)) and further an equivalent structure of a limb of the user 2.

The limb movement function evaluating system is able to configure a movement path of a limb under guidance by different types of actuators 1012. The movement path in a space can be a straight line or a closed curve, for example, circular curve, elliptic curve, figure-of-eight curve, ∞ type curve, etc., which could be either a planar movement path or a three-dimensional movement path in a space. In a round-trip movement along a straight line, endpoints will be singularity points in calculations which should be excluded from computation of a limb movement function curve. The actuator 1012 can be a straight-line linkage, ball bearings, a four-bar linkage, a linear guideway, a cam or gear wheels, each of which can move in a space. However, a movement path or the actuator 1012 is not limited to each of the above descriptions.

For the driver 1013, a mechanical impedance induced by a limb is taken as an output variation of a load to be driven (the larger a mechanical impedance, the heavier a load; the fewer a mechanical impedance, the lighter a load). The impedance detector 1014 is an electronic device with arithmetic functions, for example, a computer device, microprocessor circuits in which firmware for impedance detection is burned, or digital circuits based on Verilog or VHDL. As such, the impedance detector 1014 is able to measure signals of operating voltage or current of the driver 1013, acquire equivalent mechanical impedances for responses of a limb after analyzing a movement path of a limb of the user 2 corresponding to electrical signals in each movement cycle, and transmit measured results to the analysis device 11 for further analyses via the message communicating device 12.

Figure 3:
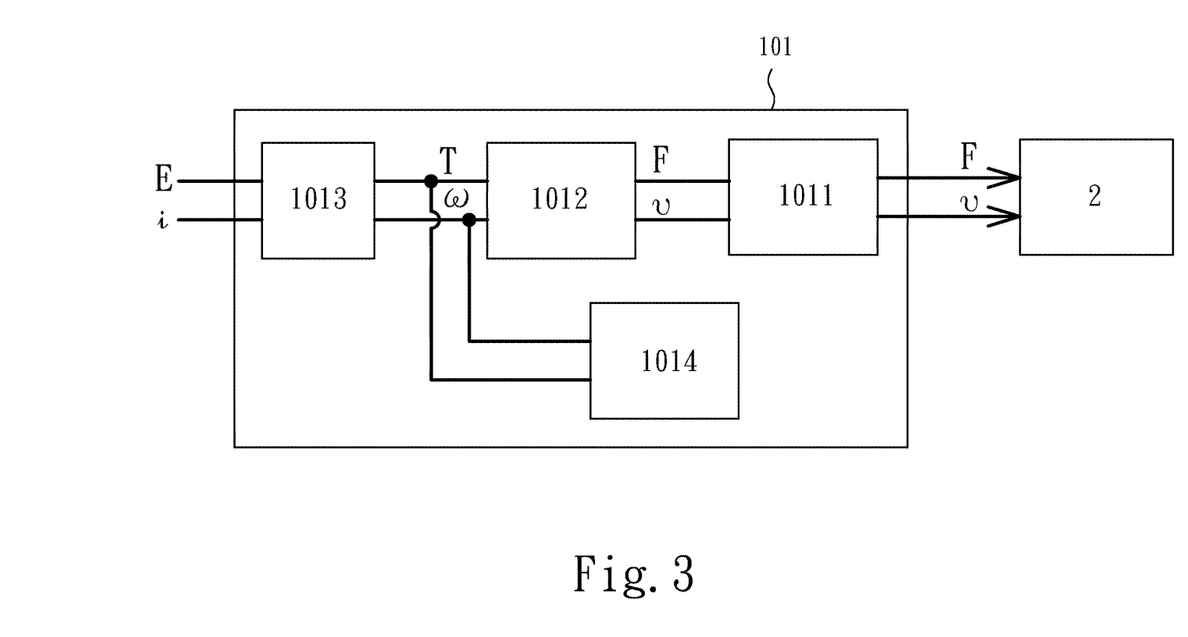
FIG. 3 illustrates an equivalent model of a limb movement function evaluating system.

Referring to FIG. 3, which illustrates an equivalent model of the limb driving subsystem 101 in the present disclosure, for descriptions of the concept of equivalent conversions. The limb driving subsystem 101 comprises the limb guiding device 1011, the actuator 1012 and the driver 1013, all of which are cascaded. Each of the limb guiding device 1011, the actuator 1012 and the driver 1013 is provided with an energy input port as well as an energy output port and energized from an output port of a preceding cascaded device by a potential variable and a flow variable at the input port. The product of a potential variable and a flow variable is input power or output power; the quotient of a potential variable divided by a flow variable is an impedance value at a port. An input impedance of the guiding device 1011, the actuator 1012 or the driver 1013 is used in determining power to be transmitted to one end at which work is done.

The driver 1013 (for example, a motor) is capable of transforming electric energy to mechanical energy. A potential variable input and a flow variable input are voltage (E) and current (I), respectively; a potential variable output and a flow variable output are torque (T) and rotary speed ($\omega$), respectively. The power transfer between inputs and outputs, which are classified into different energy domains, depends on a transduction matrix as follows:

$$\begin{Bmatrix} E \\ i \end{Bmatrix}^i = \begin{bmatrix} A & B \\ C & D \end{bmatrix}^D \begin{Bmatrix} T \\ \omega \end{Bmatrix}^{D_0} = [TD]^D \begin{Bmatrix} T \\ \omega \end{Bmatrix}^{D_0} \quad (a)$$

The actuator 1012 (for example, a gear-rack pair) is characteristic of functions as follows:

(1) Change movement induced by mechanical energy, for example, movement from rotation to linear motion; and (2) Match mechanical impedances between an energy supplier of the limb driving subsystem 101 and a limb doing work. Mechanical impedances which match each other optimize work transfer efficiency. The transmission matrix $[TM]^M$ for relationships between potential variable (flow variable) inputs and potential variable (flow variable) outputs is shown as follows:

$$\begin{Bmatrix} T \\ \omega \end{Bmatrix}^{D_0} = \begin{bmatrix} A & B \\ C & D \end{bmatrix}^M \begin{Bmatrix} F \\ v \end{Bmatrix}^{M_0} = [TM]^M \begin{Bmatrix} T \\ \omega \end{Bmatrix}^{M_0} \quad (b)$$

The limb guiding device 1011 (for example, a disc and a handle) is able to apply received energy to the second end of a limb. The transmission matrix $[TM]^G$ for relationships between potential variable (flow variable) inputs and potential variable (flow variable) outputs is shown as follows:

$$\begin{Bmatrix} F \\ v \end{Bmatrix}^{M_0} = \begin{bmatrix} A & B \\ C & D \end{bmatrix}^G \begin{Bmatrix} F \\ v \end{Bmatrix}^o = [TM]^G \begin{Bmatrix} T \\ \omega \end{Bmatrix}^o \quad (c)$$

With equations (a), (b) and (c) combined, the following relationships are presented:

$$\begin{Bmatrix} E \\ i \end{Bmatrix}^i = \begin{bmatrix} A & B \\ C & D \end{bmatrix}^D \begin{bmatrix} A & B \\ C & D \end{bmatrix}^M \begin{bmatrix} A & B \\ C & D \end{bmatrix}^G \begin{Bmatrix} F \\ v \end{Bmatrix}^o$$

As a result, the relationships between inputs and outputs of the limb driving subsystem 101 are:

$$\begin{Bmatrix} E \\ i \end{Bmatrix}^i = \begin{bmatrix} A & B \\ C & D \end{bmatrix} \begin{Bmatrix} F \\ v \end{Bmatrix}^o = [T] \begin{Bmatrix} F \\ v \end{Bmatrix}^o \quad (d)$$

The parameters of A, B, C and D in matrices of $[TD]^D$, $[TM]^M$, $[TM]^G$ and $[T]$ are derived from the relationships as follows:

$$A = \frac{E}{F}\bigg|_{v=0} \quad B = \frac{E}{v}\bigg|_{F=0} \quad (e)$$
$$C = \frac{i}{F}\bigg|_{v=0} \quad D = \frac{i}{v}\bigg|_{F=0}$$

In equation (e), the outputs of F and v are a potential variable input and a flow variable input at the second end of a limb, respectively. Because of an electric impedance of $Z^e=E/i$ and a mechanical impedance of $Z^m=F/v$, the equation (d) is changed to:

$$Z^m = \frac{DZ^e - B}{A - CZ^e} \quad (f)$$

With A, B, C and D given, the equation (f) implies a mechanical impedance of $Z^m$ at the second end of a limb is derived from an electric impedance input of $Z^e$ by means of measurement of the limb driving subsystem 101.

Figure 4A:
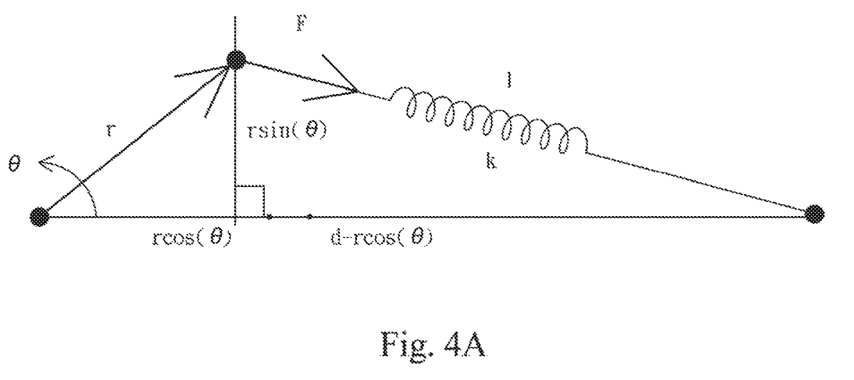
FIGS. 4A, 4B and 4C are schematic views of measurement tests.
Figure 4B:
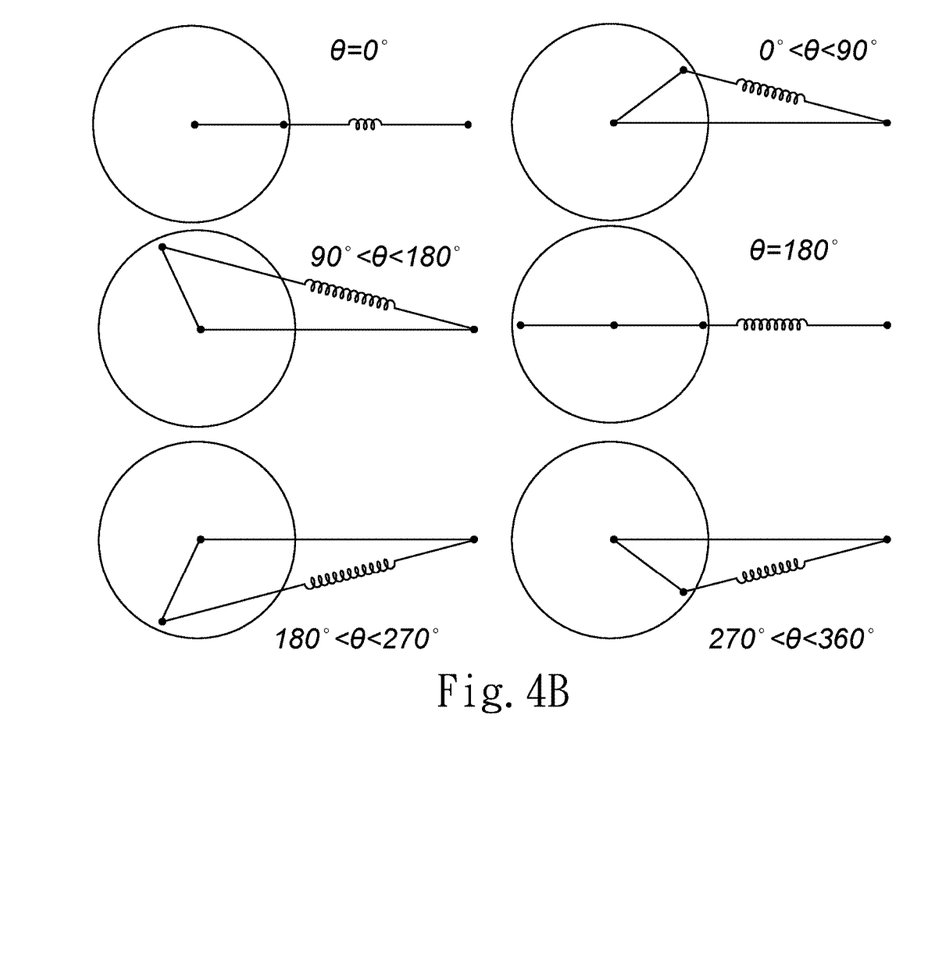
Figure 4C:
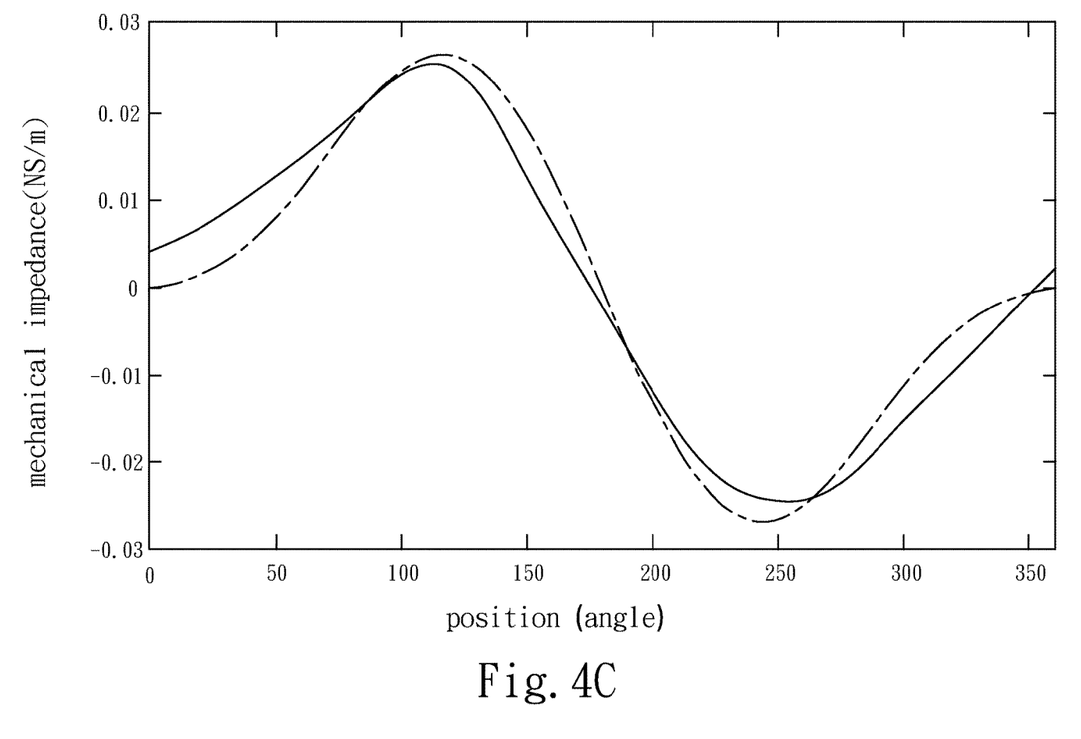

To illustrate meanings of the above equations, a spring component equivalent to a limb in the present disclosure, a DC motor (the driver 1013), a pair of gear wheels (the actuator 1012) and a disc (the limb guiding device 1011) are selected in an equivalent model as shown in FIG. 4A. In FIG. 4A, theta ($\theta$), r, F, l and k are an angle of the disc which is rotated, the disc's diameter, force applied on the spring, the length of the spring which is stretched, and the spring's elasticity coefficient, respectively. Referring to FIG. 4B, which illustrates six conditions of the disc which is rotated. FIG. 4C illustrates theoretical values (as shown in the dotted line) and measured values (as shown in the solid line) wherein the horizontal axis and the vertical axis present rotated angles and mechanical impedances, respectively. The equation to calculate theoretical torques (T) is shown as follows:

$$T = rk\left(\sqrt{r^2 + d^2 - 2rd\cos\theta} - l_0\right)\frac{d}{\sqrt{r^2 + d^2 - 2rd\cos\theta}}\sin\theta \quad (g)$$

As shown in FIG. 4C, the theoretical and measured values are approximate and the limb movement function evaluating method in the present disclosure is feasible. It should be noted that a difference between a theoretical value and a measured value is attributed to connecting components used to fix a spring and is a quantifiable and estimated value which can be eliminated in a back-end signal processing procedure.

Figure 5:
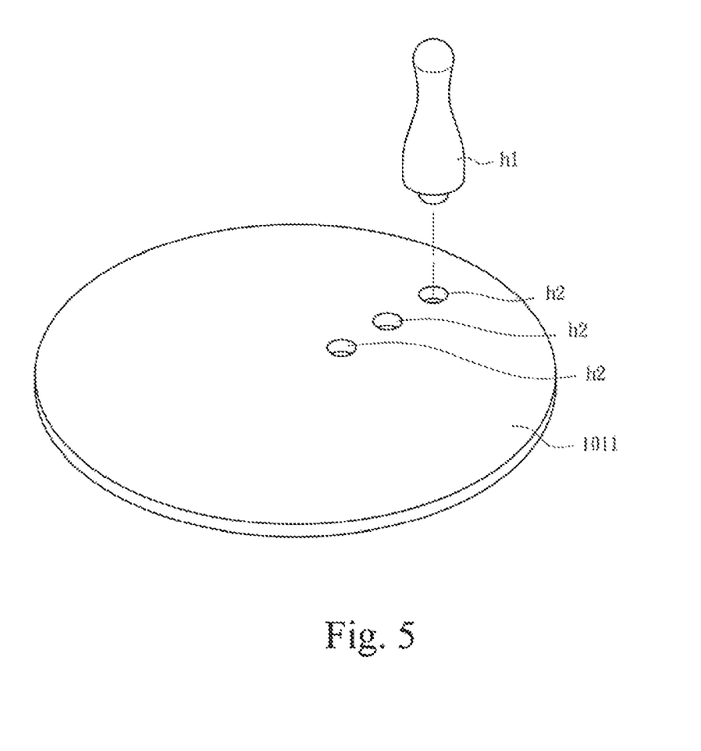
FIG. 5 is a schematic perspective view of a limb guiding device in the first embodiment.

Referring to FIG. 1, which illustrates a limb movement function evaluating method and an implantation system thereof in the first embodiment. The limb guiding device 1011 is a disc (FIG. 5). In the embodiment, the first end and the second end of a limb of the user 2 are defined as a shoulder and a palm, respectively; the limb guiding device 1011 is a circular ring or a disc with a gripping portion h1 and a plurality of pinholes h2 thereon; the gripping portion h1 can be inserted into a pinhole h2, which features a distinct radius, by the user 2 for configuration of the disc's turning radius. The actuator 1012 is a straight-line linkage with two ends pivotally linking an output shaft of the driver 1013 and a spindle of the circular ring or the disc via universal joints for development of a circular movement path of a limb of the user 2 under guidance of the limb guiding device 1011. In the course of movement, both the impedance detector 1014 and the movement function analyzer 112 will analyze an angle of the limb guiding device 1011 and a mechanical impedance corresponding to the angle to calculate a limb movement function curve, display results on the displayer 112, or transmit results to a hospital computer device from which the medical staff evaluate conditions of a convalescent and the user 2 adjusts a rotary speed of the driver 1013 for new intensity of rehabilitation according to displayed results or advices of the medical staff.

When variations of relaxing and then tightening muscles as well as measured errors are deducted from fast detected limb movement function curves by the movement function analyzer 112, accurate measurement information for analyses of current movement conditions of a limb can be provided. The displayer 112 is used in displaying measurement and analysis information for movement conditions of a limb optionally to the user 2. The user 2 who is informed of movement conditions of a limb is able to configure a running speed of the motor in the driver 1013 for new intensity of rehabilitation.

Through a communications network, the message communicating device 113 transmits data such as mechanical impedance and limb movement function curve optionally to a hospital computer device from which the medical staff 41 evaluates current conditions of a convalescent; the hospital computer device depends on evaluation results to inform the user 2 of advices on intensity of rehabilitation which is adjustably configured in the driver 1013. The communications network can be a wired communications network or a wireless communications network.

In the present disclosure, a method to measure limb movement functions in the second embodiment is applied in the limb movement function evaluating system and comprises steps as follows:

S101: Fix the first end of a limb of the user 2 at the limb movement function evaluating device 10.

S102: Guide the second end of the limb of the user 2 for movement relative to the first end.

S103: Measure corresponding mechanical impedances responding to limb movement of the user 2 at driving points.

S104: Provide a limb movement function curve according to measured mechanical impedances which correspond to a movement path of a limb of the user 2.

In the present disclosure, a computer device for analyzing limb movement functions is presented in the third embodiment. The computer device comprises a communicator and a processor linking the communicator. The communicator communicates with at least a limb movement function evaluating system. The processor accesses a plurality of limb movement function curves from the limb movement function evaluating system for statistic analyses and provides rehabilitation determining information by which a rehabilitation degree represented by the limb movement function curve is determined.

In the present disclosure, a computer device for analyzing limb movement functions is presented in the fourth embodiment. Similar to the third embodiment, the computer device for analyzing limb movement functions in the fourth embodiment further allows the medical staff to access multiple limb movement function curves from a single limb movement function evaluating system of a user for statistic analyses. To upgrade accuracy of statistics, the computer device will capture partial limb movement function curves from multiple ones transmitted by a single user, for example, 50% (from the 41st curve to the 70th curve) among 100 limb movement function curves transmitted by a single user for statistic analyses. With rehabilitation everyday completed, the user 2 or the medical staff is informed of objective real-time evaluation results from the computer device which analyzes and evaluates a rehabilitation degree of the user 2 in the same day.

In the present disclosure, a computer device for analyzing limb movement functions is presented in the fifth embodiment. Similar to the third embodiment, the computer device for analyzing limb movement functions in the fifth embodiment further allows a handheld electronic device grasped in a user such as tablet computer and smart phone to communicate with the limb movement function evaluating system for statistic analyses. As such, a user controls real-time rehabilitation progress everyday from a handheld electronic device.

In the present disclosure, a computer device for analyzing limb movement functions is presented in the sixth embodiment. Similar to the third embodiment, the computer device for analyzing limb movement functions in the sixth embodiment further allows the medical staff to access limb movement function curves of many users from which the levels of single convalescents for their limb conditions can be determined (for example, Level 1 to Level 5). As such, each user, who is operating the limb movement function evaluating system, learns the level of his/her rehabilitation status by checking relevant information.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A limb movement function evaluating system, comprising:
   a limb fixing device, configured to fix a first end of an external user limb;
   a limb guiding device, configured to guide a second end of the user limb, wherein the second end and the first end are separated by a distance;
   a driver and an actuator, wherein the actuator is configured to provide at least one movement path, and the driver further drives the limb guiding device by the actuator so as to move the second end relatively to the first end;
   an impedance detector, connected with the driver so as to measure a mechanical impedance when a movement of the user limb response to the driver;
   an analysis device, connected with the impedance detector, wherein the analysis device provides a limb movement function curve according to the measured mechanical impedance and corresponding movement path of the user limb,
   wherein the impedance detector acquires an electric variation from a measuring port of the driver, and analyzes an electric impedance at each movement cycle of the movement path of the user limb so as to calculate the mechanical impedance according to a transduction matrix of the driver, a transmission matrix of the actuator, and a transmission matrix of the limb guiding device.

2. The system as claimed in claim 1, further comprising a message communicating device connected with the analysis device, the message communicating device selectively transmitting the mechanical impedance or the limb movement function curve to an external computer device so as to trigger the computer device to analysis.

* * * * *